(12) United States Patent
Han et al.

(10) Patent No.: US 9,940,433 B2
(45) Date of Patent: *Apr. 10, 2018

(54) DISCOVERING POPULATION STRUCTURE FROM PATTERNS OF IDENTITY-BY-DESCENT

(71) Applicant: Ancestry.com DNA, LLC, Lehi, UT (US)

(72) Inventors: Eunjung Han, San Francisco, CA (US); Ross E. Curtis, Cedar Hills, UT (US); Peter Carbonetto, San Francisco, CA (US)

(73) Assignee: ANCESTRY.COM DNA, LLC, Lehi, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/458,549

(22) Filed: Mar. 14, 2017

(65) Prior Publication Data
US 2017/0242957 A1    Aug. 24, 2017

Related U.S. Application Data

(63) Continuation of application No. 15/168,011, filed on May 28, 2016.

(60) Provisional application No. 62/168,808, filed on May 30, 2015.

(51) Int. Cl.
| | |
|---|---|
| *G06F 19/14* | (2011.01) |
| *C12Q 1/68* | (2018.01) |
| *G06F 19/22* | (2011.01) |
| *G06F 19/24* | (2011.01) |
| *C40B 30/02* | (2006.01) |

(52) U.S. Cl.
CPC .......... *G06F 19/14* (2013.01); *C12Q 1/6888* (2013.01); *C40B 30/02* (2013.01); *G06F 19/22* (2013.01); *G06F 19/24* (2013.01)

(58) Field of Classification Search
None
See application file for complete search history.

(56) References Cited

U.S. PATENT DOCUMENTS

| | | | |
|---|---|---|---|
| 2013/0149707 A1* | 6/2013 | Sorenson | G06F 19/22 435/6.12 |
| 2014/0108527 A1 | 4/2014 | Aravanis et al. | |
| 2014/0278138 A1* | 9/2014 | Barber | G06F 19/14 702/19 |

OTHER PUBLICATIONS

Qian et al. Efficient clustering of identity-by-descent between multiple individuals. Bioinformatics, Dec. 19, 2013, vol. 30, pp. 915-922.*

PCT International Search Report, PCT Application No. PCT/IB2016/053166, dated Sep. 6, 2016, 13 pages.
Palin, K. et al., "Identity-By-Descent-Based Phasing and Imputation in Founder Populations Using Graphical Models," Genetic Epidemiology, Oct. 17, 2011, pp. 853-860, vol. 35.
Staples, J. et al., "PRIMUS: Rapid Reconstruction of Pedigrees from Genome-Wide Estimates of Identity by Descent," The American Journal of Human Genetics, Nov. 6, 2014, pp. 553-564, vol. 95.
Atzmon, G. et al., (2010), "Abraham's Children in the Genome Era: Major Jewish Diaspora Populations Comprise Distinct Genetic Clusters with Shared Middle Eastern Ancestry," American Journal of Human Genetics, 86(6): 850-859.
Carmi, S. et al., (2014 ), "Sequencing an Ashkenazi Reference Panel Supports Population-Targeted Personal Genomics and Illuminates Jewish and European Origins," Nature Communications 5: 4835.
Francioli, et al., (2014), Whole-Genome Sequence Variation, Population Structure and Demographic History of the Dutch Population, Nature Genetics 46(8): 1' 95.
Gauvin, H. et al., (2014), "Genome-Wide Patterns of Identity-by-Descent Sharing in the French Canadian Founder Population," European Journal of Human Genetics 22: 814' 821.
Gusev, A. et al., (2009), "Whole Population, Genome-Wide Mapping of Hidden Relatedness," Genome Research 19(2): 318' 326.
Genomes-2012] 1000 Genomes Project Consortium (2012), "An Integrated Map of Genetic Variation from 1,092 Human Genomes," Nature 491: 56-65.
Alexander, D.H. et al., (2009), "Fast Model-Based Estimation of Ancestry in Unrelated Individuals," Genome Research 19: 1655-1664.
Alexander, D.H. et al., (2011 ), "Enhancements to the ADMIXTURE Algorithm for Individual Ancestry Estimation," BMC Bioinformatics 12(1 ): 246.
Belkin, M. et al., (2003), "Laplacian Eigenmaps for Dimensionality Reduction and Data Representation," Neural Computation 15: 1373-1396.
Bengio, Y. et al., (2004), "Out-of-Sample Extensions for LLE, Isomap, MOS, Eigenmaps and Spectral Clustering," In Advances in Neural Information Processing Systems 16, p. 1621.
Blondel, V.D. et al., (2008), "Fast Unfolding of Community Hierarchies in Large Networks," Journal of Statistical Mechanics: Theory and Experiment: p. 10008.
Browning, S.R., (2006), "Multilocus Association Mapping Using Variable-Length Markov Chains," American Journal of Human Genetics 78(6): 903-913.
Browning, S.R. et al., (2007), "Rapid and Accurate Haplotype Phasing and Missing-Data Inference for Whole-Genome Association Studies by Use of Localized Haplotype Clustering," American Journal of Human Genetics 81 (5): 1084-1096.

(Continued)

*Primary Examiner* — Russell S Negin
(74) *Attorney, Agent, or Firm* — Fenwick & West LLP (57) ABSTRACT

Described are techniques for determining population structure from identity-by-descent (IBD) of individuals. The techniques may be used to predict that an individual belongs to zero, one or more of a number of communities identified within an IBD network. Additional data may be used to annotate the communities with birth location, surname, and ethnicity information. In turn, these data may be used to provide to an individual a prediction of membership to zero, one or more communities, accompanied by a summary of the information annotated to those communities.

20 Claims, 5 Drawing Sheets

(56) References Cited

OTHER PUBLICATIONS

Cann, H.M. et al., (2002), "A Human Genome Diversity Cell Line Panel," Science 296(5566): 261-262.
Carmi, S. et al., (2013), "The Variance of Identity-by-Descent Sharing in the Wright-Fsher Model," Genetics 193(3): 911-928.
Cavalli-Sforza, L.L., (2005), "The Human Genome Diversity Project: Past, Present and Future," Nature Reviews Genetics 6(4): 333-340.
Durand, E.Y. et al., (2014), "Reducing Pervasive False-Positive Identical-by-Descent Segments Detected by Large-Scale Pedigree Analysis," Molecular Biology and Evolution 31 (8): 2212-2222.
Fortunato, S. et al., (2007), "Resolution Limit in Community Detection," Proceedings of the National Academy of Sciences 104( 1 ): 36-41.
Fortunato, S., (2010), "Community Detection in Graphs," Physics Reports 486: 75-174.
Good, B.H. et al., (2010), "Performance of Modularity Maximization in Practical Contexts," Physical Review E 81 (4): 1-19.
Girvan, M. et al., (2002), "Community Structure in Social and Biological Networks," PNAS 99( 12):7821-7826.
Hao, W. et al., (2013), "Probabilistic Models of Genetic Variation in Structured Populations Applied to Global Human Studies," arXiv:1312.2041.
The International HapMap Consortium, (2007), "A Second Generation Human Haplotype Map of over 3.1 Million SNPs," Nature 449: 851-861.
Lee, A.B. et al., (2010), "Discovering Genetic Ancestry Using Spectral Graph Theory," Genetic Epidemiology 34: 51-59.
Lee, A.B. et al., (2012), "A Spectral Graph Approach to Discovering Genetic Ancestry," Annals of Applied Statistics 6(1 ): 179-202.
Meirmans, P.G., (2012), "The Trouble with Isolation by Distance," Molecular Ecology 21 (12): 2839-2846.
McGraw, P.N. et al., (2008), "Laplacian Spectra as a Diagnostic Tool for Network Structure and Dynamics," Physical Review E 77(3).
McVean, G., (2009), "A Genealogical Interpretation of Principal Components Analysis," PLoS Genetics 5(10): e1000686.
Coifman, R.R. et al., (2005), "Diffusion Maps, Spectral Clustering and Eigenfunctions of Fokker-Planck Operators," Applied and Computational Harmonic Analysis 21: 5-30.
Newman, M.E.J., (2011 ), "Communities, Modules and Large-Scale Structure in Networks," Nature Physics 8( 1 ): 25-31.
Novembre, J. et al., (2008), "Genes Mirror Geography within Europe," Nature 456(7218): 98-101.
Palamara, P.F. et al., (2012), "Length Eistributions of Identity by Descent Reveal Fine-Scale Demographic History," American Journal of Human Genetics 91 (5): 809-822.
Palamara P.F. et al., (2013), "Inference of Historical Migration Rates Via Haplotype Sharing," Bioinformatics 29(13): 180-188.
Pritchard, J.K. et al., (2000), "Inference of Population Structure Using Multilocus Genotype Data," Genetics 155(2): 945-959.
Purcell, S. et al., "PLINK: A Tool Set for Whole-Genome Association and Population-Based Linkage Analyses," American Journal of Human Genetics 81 (3): 559-575, 2007.
Raj, A. et al., (2014 ), "FastSTRUCTURE: Variational Inference of Population Structure in Large SNP Data Sets," Genetics 197(2): 573-589.
Ron, D. et al., "On the Learnability and Usage of Acyclic Probabilistic Finite Automata," J. Comp Syst. Sci., 56:133-152, 1998.
Von Luxburg, U., (2007), "A Tutorial on Spectral Clustering," Statistics and Computing 17(4 ): 395-416.
Welch, B.L., (1947), "The Reneralization of "Student's" Problem when Several Different Population Variances are Involved," Biometrika 34(1-2): 28-35.
Williams A. L. et al., (2012), "Phasing of Many Thousands of Genotyped Samples," American Journal of Human Genetics 91 (2): 283-251.
Zelnik-Manor, L. et al., (2004 ), "Self-Tuning Spectral Clustering," In Advances in Neural Information Processing Systems 17: 1601-1608.
Zhang, J., (2010), "Ancestral Informative Marker Selection and Population Structure Visualization Using Sparse Laplacian Eigenfunctions," PLoS One 5(11 ): e13734.
Zhao, F. et al., (2010), "Spectral Clustering with Eigenvector Selection Based on Entropy Ranking," Neurocomputing 73(10-12): 1704-1717.
International HapMap Consortium, "A Haplotype Map of the Human Genome," Nature. Oct. 2005 437(7063): 1299-1320.
Patterson, N, et al., "Population Structure and Eigenanalysis," PLoS Genet 2006 2(12): e190.
Purcell, S., "PLINK (1.07) Documentation," May 10, 2010, 293 pages, http://pnga.mgh.harvard.edu/purcell/plink/.

* cited by examiner

DISCOVERING POPULATION STRUCTURE FROM PATTERNS OF IDENTITY-BY-DESCENT

CROSS REFERENCE TO RELATED APPLICATIONS

This application is a continuation of prior, co-pending U.S. application Ser. No. 15/168,011, filed on May 28, 2016, which claims the benefit of U.S. Provisional Application No. 62/168,808, filed May 30, 2015, both of which are incorporated by reference in their entirety.

BACKGROUND

Field

The disclosed embodiments relate to discovering historical populations from the pattern of genetic relationships between people.

Description of Related Art

Although humans are, genetically speaking, almost entirely identical, small differences in human DNA are responsible for some observed variation between individuals. In fact, by comparing these small differences in DNA of individuals, it is possible to detect long chromosome segments suggestive of inheritance from a recent common ancestor, and then use these detected segments to estimate how closely two people are related. The process of identifying segments suggestive of recent common inheritance is known in population genetics literature as an analysis of identity-by-descent (IBD). IBD analysis can be used to predict the familial relationship between any two people (e.g., second cousins) in a population as long as the relationship is due to shared common ancestors from the recent past.

Learning about population structure from genetic polymorphism data is an important topic in genetics. The most widely used methods in this area are based on modeling variation in allele frequencies. These methods have shed light, for example, on historical patterns of migration in human populations. To take one example of this, prior genetic studies of the United States (US) have helped to elucidate the diversity of recent immigrants in relation to other parts of the world (e.g. Europe, Africa). By contrast, patterns of IBD can be used to study more recent demography of known populations, such as demographic events that have occurred within the US in the period beginning with European colonization.

While researchers have previously used analysis of IBD patterns to learn about the history of different groups of people, using IBD to discover groups within hetereogeneous populations such as the present-day US has not been done previously.

SUMMARY

Disclosed herein are techniques for determining population structure from identity-by-descent (IBD) of individuals. In various embodiments, the techniques disclosed herein may additionally be used for predicting assignments of individuals to populations based on obtained genetic information. In other embodiments, additional data is used to annotate the inferred populations, and characterize them with respect to known worldwide population structure and historical events.

In one embodiment, a process for determining IBD segments includes analyzing phased genetic data obtained from DNA samples of individuals. Phased genetic data from pairs of individuals in a sample are analyzed to estimate shared IBD chromosomal segments. The extent of IBD sharing between every pair can be mapped to an affinity metric.

These affinity metrics computed for every pair of DNA samples are used to generate an IBD network, in which nodes in the network represent individuals, and weighted edges in the network represent the IBD-based affinity between individuals. Application of a network clustering algorithm allows for the identification of structure from the pattern of IBD. Each cluster within an IBD network may define a group of people that share common ancestral origins or a common history. To characterize this shared history underlying each IBD network cluster, identified clusters are annotated with historical data based on information available about the individuals in each cluster. These annotations include, for example, genealogical data (e.g., surnames and birth locations of ancestors in pedigrees), estimates of ethnic background based on the DNA sample, and information obtained from user surveys.

In some embodiments, the IBD network may be used to construct data sets, referred to as reference panels, which can be used to train models. These models can in turn be used to generate a prediction regarding which clusters are relevant to a hypothetical user, such as a new user, based on a sample of their DNA.

BRIEF DESCRIPTION OF THE DRAWINGS

These and other features, aspects, and advantages of the present invention will become better understood with regard to the following description, and accompanying drawings, where.

Note that for purposes of clarity, only one of each item corresponding to a reference numeral is included in most figures, but when implemented multiple instances of any or all of the depicted modules may be employed, as will be appreciated by those of skill in the art.

DETAILED DESCRIPTION

I. Environment Overview

Figure 1:
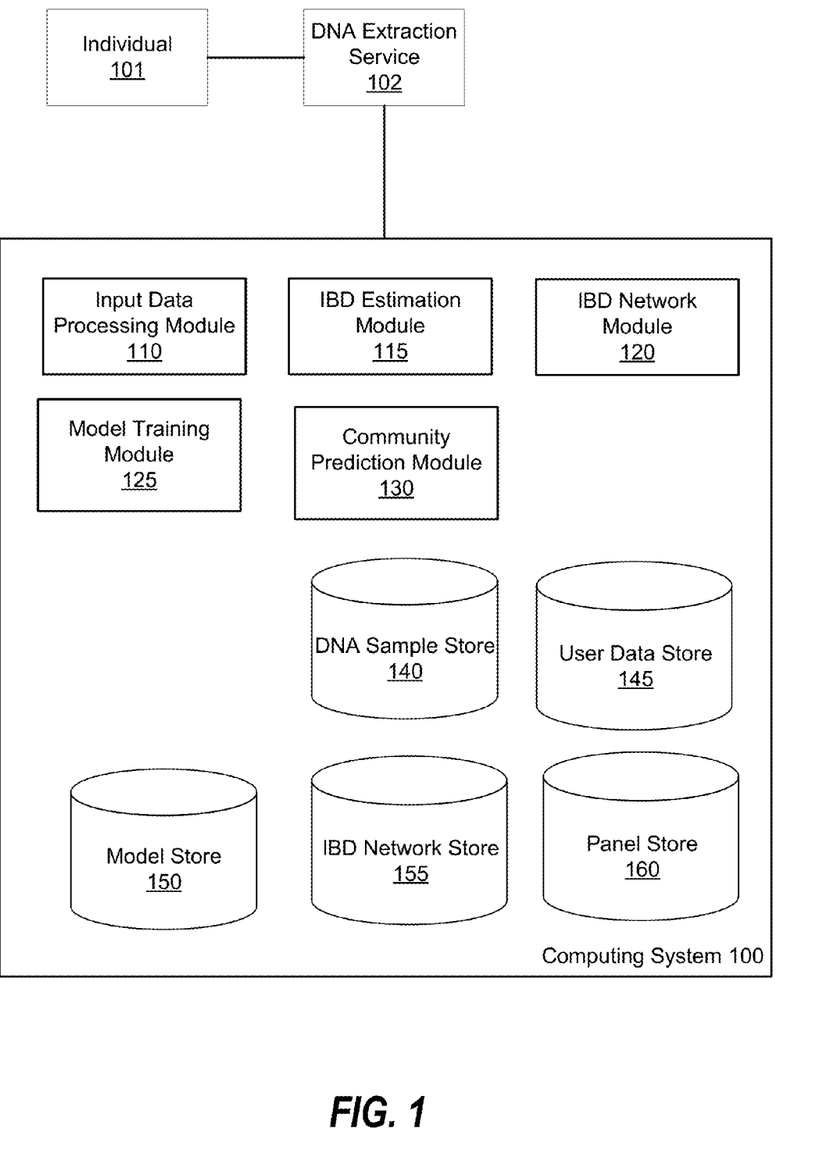
FIG. 1 is a block diagram of an overview of a computing system for estimating IBD from genotype data, using IBD to generate an IBD network and train a model based on the IBD network, according to one embodiment.

FIG. 1 is a block diagram of an overview of a computing system for estimating IBD from genotype data, using IBD to generate an IBD network and train a model based on the IBD network, according to one embodiment. Depicted in FIG. 1 are an individual 101 (i.e. a human or other organism), a deoxyribonucleic acid (DNA) extraction service 102, and a computing system 100.

Individuals 101 provide DNA samples for analysis of their genetic data. In one embodiment, an individual uses a sample collection kit to provide a DNA sample, e.g., saliva, from which genetic data can be reliably extracted according to conventional DNA processing techniques. DNA extraction service 102 receives the sample and estimates genotypes from the genetic data, for example by extracting the DNA from the sample and identifying genotype values of single nucleotide polymorphisms (SNPs) present within the DNA. The result in this example is a diploid genotype for each SNP. Computing system 100 receives the genetic data from DNA extraction service 102 and stores the genetic data in a DNA sample store 140 containing DNA diploid genotypes. In some embodiments, the genetic data stored in the DNA sample store 140 may be associated with a user in the user data store 145 via one or more pointers.

The computing system 100 processes the DNA to identify shared IBD between pairs of individuals, and uses that information to identify clusters in a sample of individuals. In one embodiment, a cluster includes individuals in a sample that exhibit a higher density of IBD connections between each other relative to other individuals in the sample. The clusters can be annotated with information about phenotypes characteristic of individuals within the group, and used to develop models that allow assignment of, often new, individuals to those clusters.

To accomplish this, the computing system 100 comprises computer program instructions that can be logically structured to generate within the processor/s and storage media of the computing system an input data processing module 110, an IBD estimation module 115, an IBD network module 120, a model training module 125, a community (cluster) prediction module 135, a DNA sample store 140, a user data store 145, a model store 150, an IBD network store 155, and a panel store 160. In other embodiments, the computer system 100 may comprise more or fewer modules, and the logical structure may be differently organized. The data stores may be represented in different ways in different embodiments, such as comma-separated text files, or as databases such as relational databases (SQL) or non-relational databases (NoSQL).

II. Input Data Processing

To process the data stored in the DNA sample store 140 and estimate IBD from the DNA samples, the computing system 100 comprises an input data processing module 110, and an IBD estimation module 115. These modules are described in relation with FIG. 2 which is a flow diagram for the operation of the computer system 100 for estimating and storing estimated IBD in accordance with an embodiment.

II.a. DNA Sample Receipt and Account Creation

Figure 2:
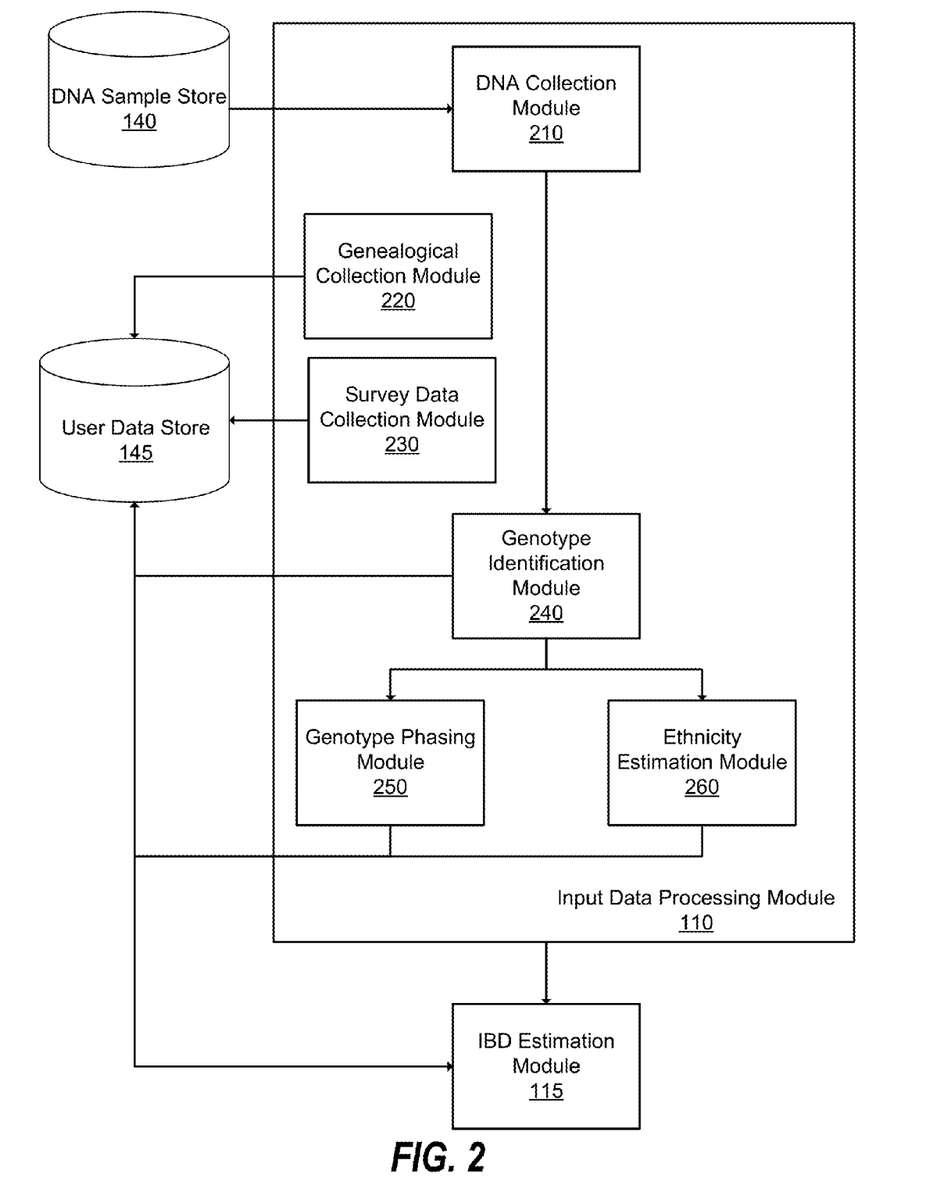
FIG. 2 is a flow diagram for the operation of the computer system for receiving, processing and storing genetic, genealogical and survey input data associated with users of the system in accordance with an embodiment.

FIG. 2 is a flow diagram for the operation of the computer system for receiving, processing and storing genetic, genealogical and survey input data. Specifically, FIG. 2 depicts an input data processing module 110, an IBD estimation module 115, a DNA sample store 140, and a user data store 145. The input data processing module 110 is responsible for receiving, storing and processing data received from an individual 101 via the DNA extraction service 102. The input data processing module 110 comprises a DNA collection module 210, a genealogical collection module 220, a survey data collection module 230, genotype identification module 240, genotype phasing module 250, and ethnicity estimation module 260.

The DNA collection module 210 is responsible for receiving sample data from external sources (e.g., extraction service 102), processing and storing the samples in the DNA sample store 140.

Although not necessarily a part of any particular illustrated module, a new user to the system 100 who is submitting their DNA among other data will activate a new account, often through graphical user interface (GUI) provided through a mobile software application or a web-based interface. As part of the account activation process, the system 100 receives one or more types of basic personal information about the individual such as age, date of birth, geographical location of birth (e.g., city, state, county, country, hospital, etc.), complete name including first, last middle names as well as any suffixes, and gender. This received user information is stored in the user data store 145, in association with the corresponding DNA samples stored in the DNA sample store 140.

The data stored in the DNA sample store 140 may store one or more received samples DNA linked to a user as a <key, value> pair associated with the individual 101. In one instance, the <key, value> pair is <sampleID, "GA TC TC AA">. The data stored in the DNA sample store 140 may be identified by one or more keys used to index one or more values associated with an individual 101. In one example, keys are a userID and sampleID, or alternatively another <key, value> pair is <userID, sampleID>. In various embodiments, the DNA sample store 140 stores a pointer to a location associated with the user data store 145 associated with the individual 101. The user data store 145 will be further described below.

II.b. Genealogical Data

The genealogical collection module 220 both receives and processes data provided by an individual for storage in the user data store 145 in association with their accounts. The genealogical collection module 220 specifically is configured to receive detailed information about an individual's family history. In some instances, family history can take the form of a pedigree of that individual (e.g., the recorded relationships in a family). To collect the data, the genealogical collection module 220 may be configured to provide an interactive GUI that asks the individual questions or provides a menu of options, and receives user input that can be processed to obtain the genealogical data. Examples of genealogical data that may be collected include, but are not limited to, names (first, last, middle, suffixes), birth locations (e.g., county, city, state, country, hospital, global map coordinates), date of birth, date of death, marriage information, family relations (manually provided rather than genetically identified), etc. These data may be manually provided or automatically extracted via, for example, optical character recognition (OCR) performed on census records, town or government records, or any other item of printed or online material.

In one or more embodiments, the pedigree information associated with a user comprises one or more specified nodes. Each specified node in the pedigree represents either the individual themselves or an ancestor of individual 101 corresponding to a stored DNA sample. Therefore, the nodes represent pedigree members that are either the individual themselves, or individuals that could have passed down generic material to the associated individual 101.

The pedigree information provided by individuals may or may not be perfectly accurate. The genealogical collection module 220 is responsible for filtering the received pedigree data based on one or more quality criteria in an effort to discard lower quality genealogical data. For example, the genealogical collection module 220 may filter the received pedigree data by excluding all pedigree nodes associated with a stored DNA sample that do not satisfy all of the following criteria: (1) recorded death date for a the linked pedigree node corresponds to official records (when available), (2) the gender is the same as the gender provided by the individual; and (3) the birth date is within 3 years of the birth date provided by the individual. It should be noted that in various instances, DNA samples that do not satisfy these criteria are still included in the subsequent analysis but either the associated pedigree data are not used, or the individual is prompted via GUI to resolve any discrepancies identified by module 220. In some embodiments, all received genealogical data marked as "private" are excluded from the any subsequent analysis to ensure that privacy requirements are met.

II.c. Survey Data

The survey data collection module 230 both receives and processes data provided by an individual for storage in the user data store 145 in association with their user accounts. The survey data collection module 230 is configured to receive information provided by individual in response to survey questions that ask about phenotypes that fall outside of those collected by the genealogical collection module 220.

Examples of survey questions include questions about an individual's phenotype, such as physical traits (e.g., height, hair, skin pigmentation, freckling, bitter taste, earlobe type, iris patterns, male pattern baldness, hair curl), wellness phenotypes (e.g., lactose tolerance, caffeine consumption, malaria resistance, norovirus resistance, muscle performance, alcohol flush), and personal preferences (e.g., likes and dislikes).

II.d. Processing and Phasing DNA Samples

The genotype identification module 240 accesses the collected DNA data from the DNA collection module 210 or the sample store 140 and identifies autosomal SNPs so that the individual's diploid genotype on autosomal chromosomes can be computationally phased. For example, for one individual 633,299 autosomal SNPs may be identified to estimate genotype phase. The genotype identification module 240 provides the identified SNPs to the genotype phasing module 250 which phases the individual's diploid genotype based on the set of identified SNPs. The genotype phasing module 250 is further described below.

As discussed immediately above, the genotype phasing module 250 generates a pair of estimated haplotypes for each diploid genotype. The estimated haplotypes are then stored in the user data store 145 in association with the user, and may also be stored in association with or verified against the genotypes of the individual's parents, who may also have their own separate accounts in the computing system 100.

A variety of different computational phasing techniques may be used including, for example, the techniques described in U.S. Patent Application No. 2016/061,568, filed on Jan. 17, 2014, which is hereby incorporated by reference in its entirety. The phasing module 250 stores phased genotypes in the user data store 145.

II.e. Ethnicity Estimation

The ethnicity estimation module 260 is responsible for estimating the global ancestral origins ("ethnicity") from an individual's SNP genotypes. In the genetics literature, this is often described as using genetic polymorphism data to estimate the proportion of the genome that is attributed to two or more defined ancestral populations. The ethnicity estimation module 260 accesses as input the diploid genotype of an individual from the genotype identification module 240 or the DNA sample store 140. Information may also be accessed that includes reference data that provide population-specific statistics to assist in the computation of the ethnicity estimates. Specifically, the reference data may include reference features such as population-specific SNP allele frequencies for one or more defined ancestral populations.

The ethnicity estimate module 260 compares the individual's diploid genotype against the reference features to estimate the degree of overlap between the two sets. In one embodiment, if there is a threshold amount of overlap between a section of one of the chromosomes of the individual and that of one of the reference features, the individual may be labeled with the ethnicity associated with the at least partially overlapping reference feature. The labeling may also occur if a sufficient number of reference features are partially overlapping, or based on the extent of overlap. The ethnicity estimate output of the ethnicity estimation module 260 algorithm takes the form of a vector of estimated ethnicity proportions of length K, where K is the number of ancestral populations under consideration. Since these are proportions, each vector entry is a number greater than or equal to 0, and all the entries of the vector sum to 1. To take a simple example of K=3 ancestral populations corresponding to African, European and Native American, it is not unusual for a user of Mexican origin to have nonzero estimated ethnicity proportions for all three ancestral populations, with an estimate such as [0.05, 0.65, 0.30], indicating that the user's genome is 5% attributed to African ancestry, 65% attributed to European ancestry and 30% attributed to Native American ancestry. The ethnicity estimation module 260 stores the estimated ethnicities in the user data store 145 in association with a particular user.

Various techniques may be used to generate the ethnicity estimate. In one embodiment, the ethnicity estimation module 260 estimates ethnicity using the techniques further described in U.S. patent application Ser. No. 14/020,577 filed on Sep. 6, 2013, which is hereby incorporated by reference in its entirety. In other embodiments, the ethnicity estimation module 260 estimates ethnicity using any one of a number of techniques, such as the STRUCTURE or ADMIXTURE algorithms. In one embodiment, the ethnicity estimation module 260 uses haplotype data to improve the accuracy of ethnicity estimate which is further described in U.S. Patent Application No. 62/191,968 filed on Jul. 13, 2015, which is hereby incorporated by reference in its entirety.

II.f. IBD Estimation

The IBD estimation module 115 is responsible for identifying IBD segments (also referred to as IBD estimates) from phased genotype data (haplotypes) between pairs of individuals stored in the user data store 145. IBD segments are chromosome segments identified in a pair of individuals that are putatively inherited from a recent common ancestor. Typically, individuals who are closely related share a relatively large number of IBD segments, and the IBD segments tend to have greater length (individually or in aggregate across one or more chromosomes), while individuals who are more distantly related share relatively few IBD segments, and these segments tend to be shorter (individually or in aggregate across one or more chromosomes). For example, while close family members often share upwards of 71 cM of IBD (e.g., third cousins), more distantly related individuals may share less than 12 cM of IBD.

In one embodiment, the IBD estimation algorithm used by the IBD estimation module 115 to estimate (or infer) IBD segments between two individuals is as described in U.S. patent application Ser. No. 14/029,765, filed on Sep. 17, 2013, which is hereby incorporated by reference in its entirety. Another further processing step may be performed on these inferred IBD segments by applying the technique described in PCT Patent Application No. PCT/US2015/055579, filed on Oct. 14, 2015, which is hereby incorporated by reference in its entirety. The identified IBD segments are stored in the user data store 145 in association with the user.

The IBD estimation module 115 is configured to estimate IBD segments between large numbers of individuals stored in the user data store 145. That is, between each individual and many other individuals in the user data store 145. These IBD estimates are used in aggregate to build IBD networks as described in Section III below. The exact extent to which IBD calculations are performed (i.e., between every pair of users vs. between only a subset of pairs of users) depends on the implementation. In one embodiment, IBD estimates between any given pair of users may only be calculated if some prior information is known (e.g., genealogical, genetic) that links them, or if an initial pre-calculation suggests there will be at least a threshold amount of IBD sharing between the pair. The selective calculation of IBD estimates described above may help reduce processing time required to identify IBD segments.

In some embodiments of this module, the computing system has been optimized to efficiently handle large amounts of IBD data. Said another way, IBD is estimated across a large number of individuals based on their DNA. For example, in one implementation, the IBD estimation module 115 (and computing system 100 generally) distributes IBD computations over a Hadoop computing cluster, internal to or external from computing system 100, and stores the phased genotypes used in the IBD computations in a database so that IBD estimates for new accounts/individuals can be quickly compared to previously processed individuals.

III. IBD Networks

Figure 3:
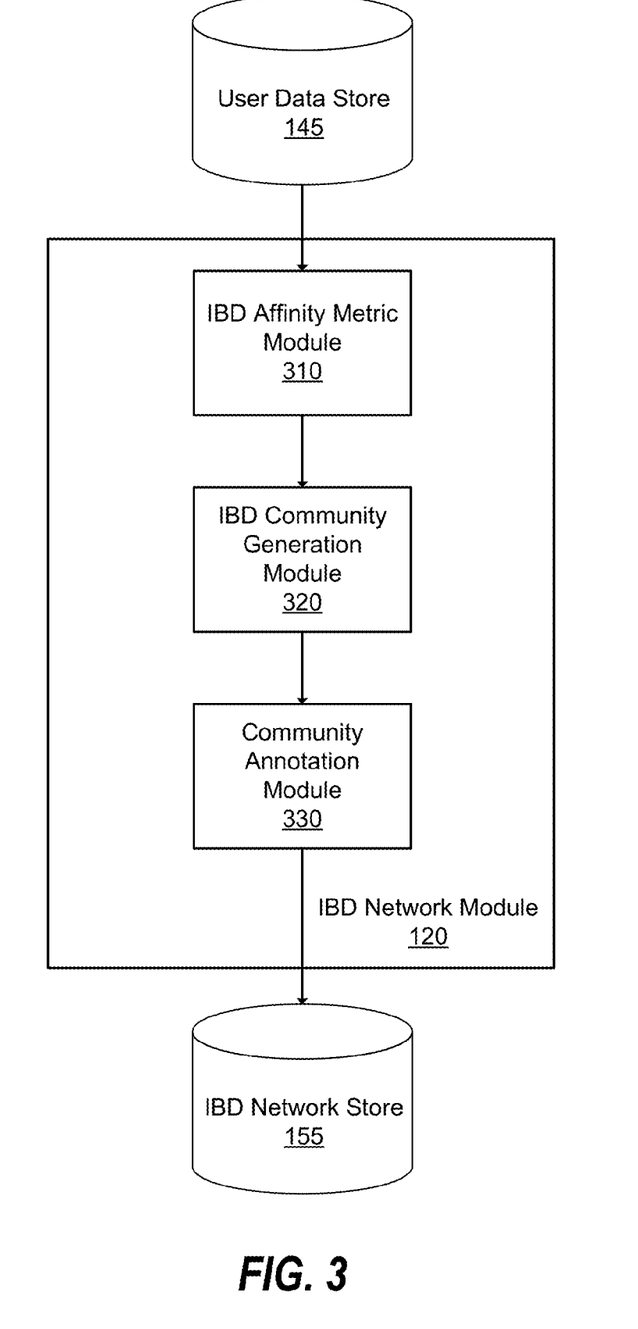
FIG. 3 is a flow diagram for constructing an IBD network, inferring clusters in the network, and annotating the IBD network clusters, in accordance with an embodiment.

FIG. 3 is a flow diagram for constructing an IBD network, inferring clusters in the network, and annotating the IBD network clusters, in accordance with an embodiment. These techniques are carried out by the IBD network module in conjunction with the user data store 145 and the IBD network store 155. In one embodiment, to accomplish these tasks the IBD network module 120 itself comprises an IBD affinity metric module 310, an IBD community generation module 320, and a community annotation module 330.

III.a. Constructing the IBD Network

The IBD affinity metric module 310 accesses estimated IBD segments from the user data store 145 in order to generate an IBD network (also referred to as an IBD graph). It should be noted that, as used herein, the terms cluster and community are used interchangeably. That is, both the terms cluster and community refer to a subset of nodes in a determined IBD network. In various embodiments, the set of clusters in the IBD Network are identified by selecting clusters that maximize the modularity objective defined with respect to the IBD network. Clusters identified from a network in this way are often referred to as "communities" in the network analysis literature; for instance, see M. E. J. Newman, *Nature Physics*, 2012 (doi:10.1038/nphys2162). Although modularity-maximizing algorithms may be employed to identify clusters in one or more embodiments, the term "community" is not used in the strict technical sense of a modularity-maximizing clustering, but is instead used more generally to refer to clusters identified in a network by taking any one of several existing network clustering approaches developed in the network analysis or machine learning areas.

The IBD network includes a number of nodes with one or more weighted edges connecting some of the nodes to each other. Each node corresponds to one of the individuals from the user data store 145. Each edge between one node and another node has a weight, a numerical value, based on the IBD estimate between the two nodes, as generated by IBD estimation module 115.

More specifically, the IBD affinity metric module 310 defines a mapping (also called an "affinity measure") from the total length of the shared IBD segments between two individuals (e.g., i and j) to the weight of the edge linking nodes i and j in the network. In one or more embodiments, the affinity measure is a real number between 0 and 1. For example, if the total length of the shared IBD segment between nodes i and j is greater than 65 cM (e.g., third cousins), then the edge linking nodes i and j receives a value of 0.97 or greater. Alternatively, if the total length of the shared IBD segment is 4-10 cM or less (e.g., distantly related or distant cousins), the edge may receive a weight of 0.

The mapping function between IBD estimates and edge weights may be any continuous or discontinuous function with the function domain defined by the set of possible total IBD length estimates. In one specific embodiment, the IBD affinity metric module 310 maps the total IBD segment lengths to edge weights by: (1) choosing a target range of generations; (2) empirically assessing, using a reasonably realistic simulation, the distribution of total IBD lengths among pairs of individuals that share common ancestors within that range of generations; and (3) defining the affinity metric so that high weights are placed on total IBD lengths arising from familial relationships sharing common ancestors corresponding to the chosen range of generations. This has the effect of more heavily weighting the edges between relatives sharing common ancestors in the target generation range; e.g., for a generation range of 0-4 generations ago, more weight is assigned to edges between relatives separated by eight meiosis events or less, and less weight is placed on nine meiosis events and more distantly related connections, where one meiosis event corresponds to a parent-child relationship, two meiosis events corresponds to siblings or to a grandparent-to-child-relationship, and so on.

In one embodiment, the IBD-to-edge-weight mapping function was chosen based on a Beta cumulative density function (CDF) (i.e., Probability (X≤x), where x is the IBD estimate between any pair of individuals) with scale parameters $\alpha=1.1$ and $\beta=10$ which defines the weights for all edges in the IBD network. It should be noted that other choices for the mapping from total IBD length to edge weight may result in the generation of an IBD network with different characteristics. For example, placing greater weight on more distant familial relationships might reveal structure arising from population events at different time periods.

III.b. Inferring Communities

The IBD community generation module 320 partitions the IBD network generated by the IBD affinity metric module 310 into two or more communities. Various algorithms may be used to cluster the IBD network. Examples are algorithms that have been developed in statistical physics and machine learning to identify "strongly connected" subsets of a network, in which the density of edges within each subset is much higher than expected. Described, below, is just one method by which clusters may be identified in an IBD network. Examples of alternative network clustering algorithms include spectral graph clustering methods. In various embodiments, communities may be detected using other clustering algorithms such as Locally Linear Embedding or Normalized Cuts.

In one embodiment, the IBD community generation module 320 identifies the communities through recursive application of the multi-level Louvain method, which is a modularity-optimization-based community detection algorithm (also called "community detection"). In other embodiments, communities may be identified via recursive application of a community detection algorithm other than the Louvain method.

In an implementation using the Louvain method, the IBD community generation module 320 identifies a high-modularity partition of the network by recursively applying the Louvain method to IBD network S comprising nodes N connected to each other via edges M each having a weight. In the Louvain method, the degree of modularity, Q, of a network partitioning is defined according to:

$$Q = \sum_k \sum_{(i,j) \in S_k} a_{ij} - \frac{d_i d_j}{2m} \quad (1)$$

where k is the community index, $S_k$ is the set of edges among all nodes assigned to community k, $a_{ij}$ is the weight of edge (i, j), $d_i$ is the "degree" of node i, defined to be the sum of all edge weights for edges connecting node i, and m is the sum of all "degrees". The computation time associated with community detection grows linearly with the number of edges, M (i.e., O(M)). The Louvain algorithm heuristically maximizes the modularity Q associated with a network S.

The community detection algorithm divides network S comprising N nodes into C communities. The partitioning of the network into communities using the Louvain method described above is denoted $(A_1, A_2, A_3, \ldots, A_C)$. Following completion of the community detection algorithms, communities $(A_1, A_2, A_3, \ldots, A_C)$ are labeled as a "valid" if they each comprise a given threshold number of nodes t. A community $A_i$ with less than the threshold number of nodes is not considered a valid community (i.e., an "invalid" community) and is, thus, omitted from subsequent steps of the community detection analysis and model training (its constituent nodes are left to stand alone without being labeled as a community). In one embodiment, the threshold number of nodes t is 1,000. However, in other embodiments the threshold number is any integer number of nodes greater than 0. The set of communities labeled as valid are denoted by $(A'_1, A'_2, A'_3, \ldots, A'_C)$, where C' is less than or equal to C.

This threshold cutoff for performing the community detection algorithm again within a community helps ensure that any detected communities will contain a large enough number of nodes to be interpreted as a group of historical or geographic significance. If a community has below the threshold number of nodes t, there is a sufficiently high likelihood that any identified subcommunities that could be generated through another application of the community identification algorithm would potentially over-fit/over-analyze the data and suggest a subpopulation that does not have an analog that experts in the field would recognize. The threshold number of nodes may be anywhere between 1000 and 10,000, depending upon the exact implementation of the system.

Once a set of valid communities is determined, the IBD community generation module 320 applies the community detection algorithm (e.g., Louvain method) again on each IBD sub-network defined by the nodes in community $A_i'$ to identify sub-communities within each community $A_i'$. To distinguish the initial set of communities from the sub-communities, the initial set of communities are called "level 1" communities, and the sub-communities are called "level 2" communities, to connote the fact that these communities can be viewed as hierarchical sets of clusters.

To identify a sub-community for each level 1 community $A_i'$ (i=1, 2, . . . , C'), the IBD community generation module 320 performs two steps. First, the IBD community generation module 320 generates a subgraph $g_i$ for each community $A_i'$ in the set of communities $A_i'$ (i=1, 2, 3, . . . , C'). The subgraph $g_i$ is defined by the subset of nodes n that are assigned to a community $A_i'$ and the subset of edges m such that (i, j) is included in the subset if and only if both i and j are assigned to community $A_i'$.

Next, the IBD community generation module 320 applies the Louvain method (or another community detection method) on the subgraph $g_i$ associated with the community $A_i'$. For example, if a level 1 community $A_1'$ is associated with a subgraph $g_1$, the Louvain method is applied to the subgraph $g_1$. After applying the community detection algorithm to each subgraph $g_i$, with i=1, 2, . . . , C', the result is a set of sub-communities $(B_1, B_2, \ldots B_D)$, where D is the total number of sub-communities identified in all of the subgraphs. D must be greater than or equal to 2C'. Similar to before, only "valid" communities exceeding a previously specified size are retained (and this may be a different (second) threshold than the (first) threshold t used for determining the level 1 communities), resulting in a final set of level 2 communities, sub-communities $(B'_1, B'_2, \ldots B'_{D'})$, in which D' is less than or equal to D.

The process described above may be repeated for subsequent levels of communities as long as at least one community has greater than the threshold number of nodes t as introduced above. For example, communities at level 3 may be delineated by module 320 by once again generating a subgraph $g_i$ for each level 2 community $B_i$ and applying the Louvain method to each subgraph $g_i$.

Following this description, an example pseudocode for the IBD community generation module 320 is as follows:
procedure community(S)
C←Louvain(S)//Identify set of communities associated network S
for each $A_i$ in C do
   if(Size($A_i$)≥1,000) then
     $g_i$←buildSubgraph(S, $A_i$)
     C←concatenate(C, community($g_i$))
return C //C is an array of communities and sub-communities associated with network S, which can be interpreted in a hierarchy of clusters.

The procedure delineated through the example pseudocode above results in a hierarchy of communities by recursively fragmenting or subdividing groups of connected nodes. The algorithm illustrated by the pseudocode above automatically stops subdividing further when the size of the subnetwork defined by a community contains fewer than 1,000 nodes.

Figure 4:
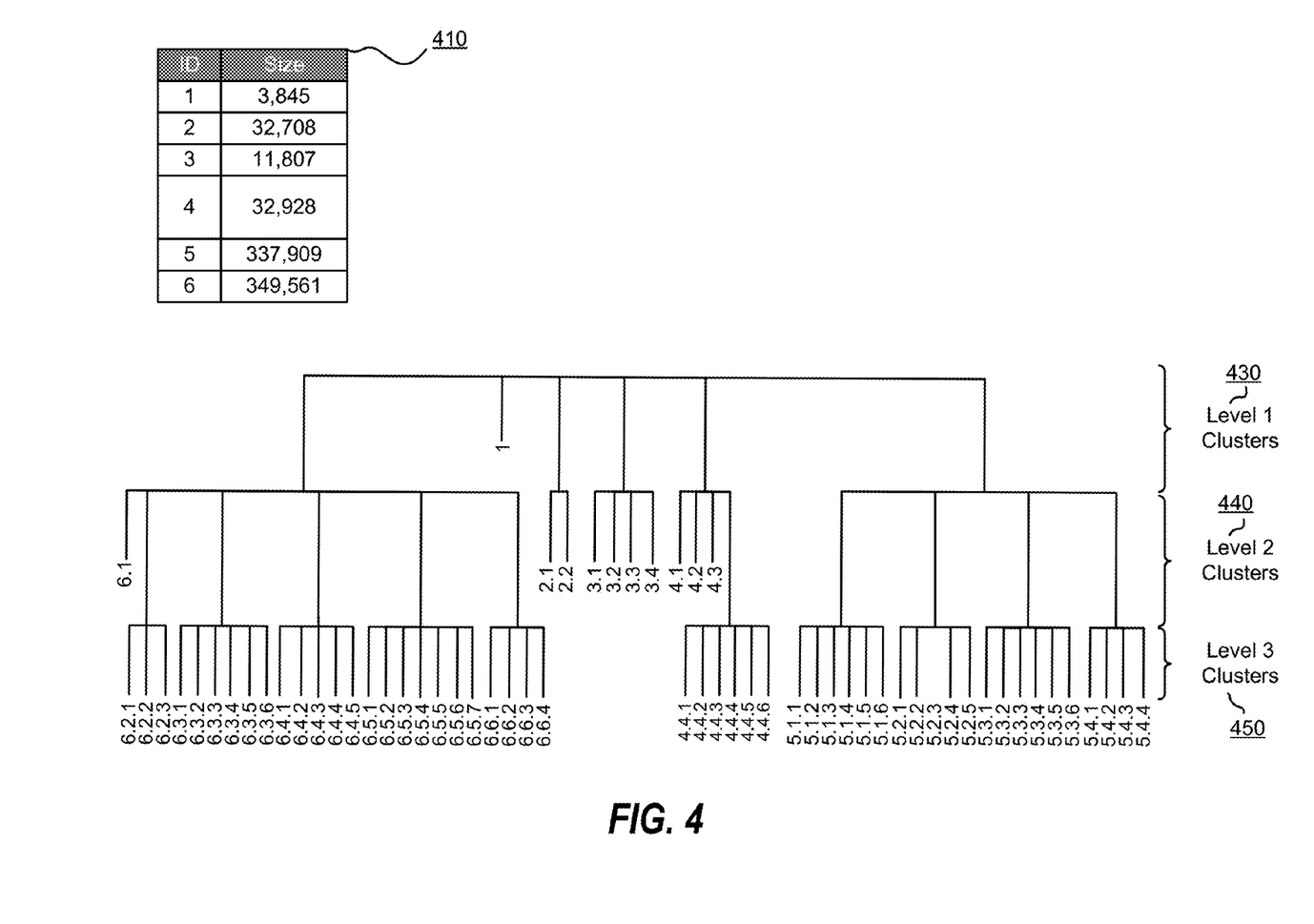
FIG. 4 is an illustration of an example result of running a hierarchical clustering algorithm on an IBD network, in accordance with an embodiment.

FIG. 4 is an illustration of an example result of running a hierarchical clustering algorithm on an IBD network, in accordance with an embodiment. Example IBD network 410 has six level-1 communities and an illustrated number of nodes in each level 1 community. Further illustrated is how the hierarchical clustering algorithm can be applied to subdivide five out of the six level 1 communities 430 into twenty level 2 communities 440, and further subdivide these into fifty level 3 communities 450, however in practice the exact community structure may vary.

III.c. Annotating IBD Communities with Genealogical Data

Returning now to FIG. 3, the community annotation module 330 is responsible for annotating a community $A_i$ with information drawn from the individuals that make up each community, such as ethnicity estimates, surnames, birth locations of the individuals or their ancestors, and responses to survey questions. The following paragraphs explain ways in which the community annotation module 330 compiles these annotations into distinguishing features that may be used to suggest a demographic or geographic interpretation of each community.

One type of annotation is provided by the ethnicity estimation module 260. In one embodiment, the ethnicity-based annotations can be used to estimate which ancestral populations are over-represented or under-represented by the individuals from the set of nodes comprising a given community. In some cases, communities with highly over-represented ancestral populations can be related to known human population structure when the interpretation of the ancestral populations is known in advance. For example, in one embodiment, communities corresponding to recent US immigrant groups such as Finnish, Jewish and Irish can be identified from the ethnicity-based annotations because some of the ancestral populations in the ethnicity estimation are defined for Finnish, Jewish and Irish. In one specific embodiment, the ethnicity-based annotations are summarized into a convenient form by compiling, for each ancestral population, the distribution of estimated ethnicity proportions among all individuals assigned to the community, and comparing against the distribution of estimated ethnicity proportions among individuals that are not assigned to the community.

Other embodiments may use alternative or more complex algorithms for summarizing the ethnicity estimates within a community, and may limit which nodes are considered in the calculation of the ethnicity-based annotations. For example, an ethnicity-based summary for a community may be determined based on the ethnicity estimates only for network nodes associated with individuals having birth dates within a specified range of years in order to better summarize the ethnic diversity of individuals from certain generations.

Another type of annotation provided by the community annotation module 330 comprises birth locations of ancestors associated with individuals assigned to a community, which can provide useful geographic clues relating a community to historical populations. To do this, the community annotation module compiles statistics from the ancestral birth location data specific to each community.

In one embodiment, the community annotation module 330 may summarize the birth location data so that it may be visualized in a graphical map format. This is accomplished, for example, by converting each birth location, within a specified range of generations, to the nearest coordinate on a two-dimensional (2-D) grid, with grid points every 0.5 degrees of latitude and longitude. Then the location of each grid point plotted on the map is the mean latitude and longitude over all the annotations assigned to that grid point.

The community annotation module 330 computes, for each grid point in the 2D grid, an odds ratio (OR). The OR is defined as the odds that a given grid point of the 2-D grid is associated with a community member over the odds that the same grid point is associated with a user who is not a member of the community. Using this OR measure, the community annotation module 330 generates a graph (or plot) that visually depicts grid points in which the largest odds ratios are indicated visually by labels or distinguishable colors, for example. In this way, the highlighted graphical map locations correspond to geographic locations that are disproportionately represented in a given community. For example, the birth locations of ancestors 0-5 generations ago associated with the Utah cluster are more highly concentrated in Utah, and this is reflected in this visual summary by map locations with particularly high odds ratios.

The community annotation 330 may then use the labels associated with specific geographic locations in the plot as an input to determine which of those geographic location labels are annotated and stored in association with the community in one of the data stores. The graphical maps and plots described above are useful because in various implementations they may be presented to a user via a GUI. However, actual generation of the graphical maps and plots is not strictly necessary in order to determine the geographic locations to annotate to a given community. The description above may be accomplished entirely through non-graphical means, that is by grouping data by geographical location, computing odds ratios based on the groups, and performing statistical analysis on the result to determine the labels.

In addition to an ethnicity and geographic origins, the community annotation module 330 may use surname annotations to generate additional historical or geographic clues about a community. To summarize surnames for a given community, the community annotation module 330 collects all surnames of recent ancestors (e.g., born after 1900 A.D.) associated with individuals who are assigned to the community. To highlight surnames that are more likely to be characteristic of the community, and therefore more likely to yield informative clues about the historical or demographic significance of the community, for each identified surname, in one embodiment, the community annotation module 330 quantifies the statistical evidence (e.g., p-value) that a given surname is over-represented in a given community compared against the background surname distribution over all individuals included in the generated IBD network. The community annotation module 330 ranks the surnames according to the statistical evidence (e.g., smallest p-values), and selects the 10 most highly ranked surnames as surnames that are characteristic to the given community. For example, the most highly ranked surnames from the surname annotations associated with individuals assigned to an Irish community include "McCarthy", "Sullivan", "Murphy", "O'Brien", and "O'Connor".

The community annotation module 330 may similarly annotate a given community using other items of data associated with the individuals assigned to that community as collected by either the genealogical collection module 220 or the survey data collection module 230, such as marriage data and responses to survey questions.

The community annotation module 330 performs annotation on many if not all communities in the IBD network. If the communities are arranged in a hierarchy (e.g., through recursive application of the Louvain method), then this may include communities at any level of the clustering hierarchy (level 1, level 2, level 3, etc.). The resulting summary for each community compiled from the annotations are stored in the IBD network store 155.

IV. Generating a Model to Classify Individuals into Communities

Figure 5:
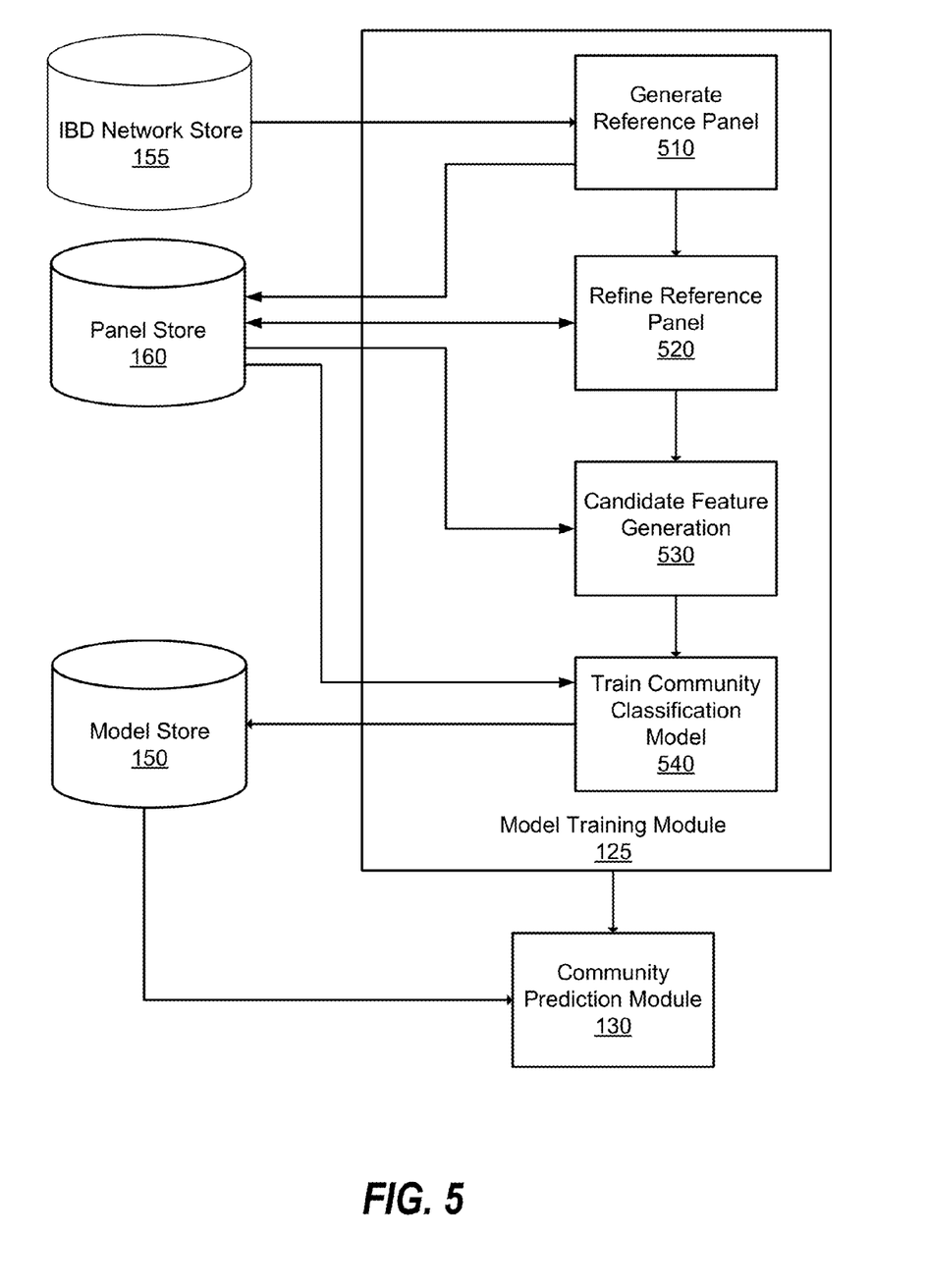
FIG. 5 is a flow diagram for generating a model to predict which individuals are assigned to which clusters, in accordance with an embodiment.

FIG. 5 is a flow diagram for generating a model to assign individuals to communities, in accordance with an embodiment. In FIG. 5, the model training module 125 accesses communities (e.g., generated as described in Section III) from the IBD network store 155 and uses the communities to build a model that can be later used to predict which community, or communities, an individual belongs to based on their DNA sample. This process is applied to all communities identified in the IBD network, after removing communities that do not satisfy additional criteria for being "valid". In cases where the communities can be viewed as a hierarchy, in which each level of the hierarchy subdivides the communities from the previous level, this process can applied to all communities at all, or selected, levels of the hierarchy.

To do this, the model training module 125 generates 510, for each community stored in the IBD network store 155, a reference panel 510, refines 520 the generated reference panel, generates one or more candidate features 530 that may be useful for predicting whether a given user is or is not a member of a given community based on the refined reference panels, and trains 540 a community classification model using the selected features and the refined reference panels. For clarity of terminology, this is described as a multi-way classification problem, in which each user may be classified into zero, one or more communities. Since each community assignment can be considered as a separate classification problem, a "model" refers to the classification of a single community, and is trained separately from other models. Therefore, the training process results in a collection of models that are configured to predict whether or not a given individual belongs to each community. Once the models have been trained on the reference panel data, the community prediction module 130 can use the model to predict which, if any, communities, a new user 101 is a member of based on the new user's genetic sample. The system 100 can use these community predictions to provide a report detailing the individual's predicted community membership without needing to re-build the IBD network or re-train the model.

IV.a. Generating Reference Panels

The model training module 125 receives from the IBD network store 155 a set of communities (or, equivalently, clusters) previously identified in an IBD network and generates a reference panel 510 for each community. To generate 510 the reference panels, the model training module 125 may simply identify all of the individuals in a community. Alternatively, module 125 may generate the reference panel based on some subset thereof. For example, a generated reference panel 510 comprises a subset of individuals selected uniformly at random from the set of individuals (network nodes) assigned to a given community. In one embodiment, a generated reference panel 510 may be limited to those individuals in a community by their birth locations, or the birth locations of their ancestors or descendants. As another example, a generated reference panel may include individuals from a community who also have West African ancestry based on their ethnicity estimates. The generated reference panels are stored in the panel store 160 in association with a particular community as stored in the IBD network store 155.

IV.b. Refining the Generated Panels

The model training module 125 refines 520 the generated 510 reference panels in an effort to remove individuals who are less representative of the community. In one embodiment, to refine a given reference panel $R_i$ (i=1, 2, . . . , P), where P is the total number of reference panels), the IBD community generation module 320 is used to run a community detection algorithm (e.g., Louvain method) on a random subgraph consisting of randomly selected set of individuals (i.e., nodes) and the IBD connections between these individuals (i.e., the weighted edges of the network). The model training module 125 repeats the process described above a number of times (e.g., 20 times) separately on each random subgraph. Note that the subgraphs must be large enough that each individual in the full IBD network is included multiple times in the subgraphs. In this analysis, the number of times individual i is assigned to the same community provides a way of ranking the "stability" of the clustering for individual i. Note that the concept of "same community" is not completely well-defined because application of the clustering algorithm to random subgraphs can produce different numbers of communities, but for simplicity the model training module 125 can consider the subset of communities that have some threshold degree of overlap in terms of the proportion of individuals assigned. In cases where a hierarchical clustering approach is implemented, this stability analysis is restricted to communities at the same level of the hierarchy. In an embodiment, individuals with a stability ranking greater than a certain threshold number (e.g., 10) are excluded from the reference panel $R_i$.

IV.c. Candidate Feature Generation

The model training module 125 uses the refined reference panels to select features that will be subsequently used to train the models introduced above. The set of candidate features included in the selection step are all defined as counts of the number of connections between a given individual and all individuals included in a reference panel, restricted to connections within a given edge weight interval or, equivalently, within a given range of estimated total IBD shared. For simplicity of terminology, each feature thus represents some "degree of connectedness" between an individual and a set of individuals included a given reference panel. There is a different set of such features for each reference panel. Therefore, the total set of candidate features includes a feature for each edge weight interval and for each reference panel. For example, supposing that the edge weights are subdivided into 6 intervals, and 300 reference panels have been generated, then a total of 1,800 candidate features are included in the feature selection step.

In one embodiment, in addition to candidate features based on number of IBD connections to a reference panel, additional candidate features may be defined based on ethnicity estimates generated for an individual by the ethnicity estimate module 260.

IV.d. Selection of Most Predictive Features

However, not all defined candidate features are useful for predicting whether or not a given user is a part of a given community. Therefore, to prevent generation of overly complex models that use less informative features ("overfitting"), and to improve the computational speed and efficiency of the trained models for generating individual predictions in the community prediction module 130, the training module 540 first selects, for each community, candidate features that are estimated to be most predictive of the assignment of an individual to a community.

To estimate which features are most predictive of community assignment, the model training module 125 runs a feature selection algorithm to estimate the prediction ability of each feature, where the prediction ability is represented as a numerical value, often normalized within the range of 0 to 1. Examples of algorithms that may be used to implement the feature selection include, but are not limited to, sparse penalized regression (e.g., Lasso), a forward/stepwise regression method, recursive feature elimination, and regularized trees.

For a given community, the input data to the feature selection algorithm are the computed values of the candidate features for all individuals in all reference panels, and an additional binary ("0" or "1") training label for each individual indicating whether or not it has been assigned to the given community. An individual in a reference panel belonging to the given community is assigned a label of "1", and an individual in a reference panel that does not belong to the same community is assigned a label of "0". In one embodiment, the input data are the computed feature values and labels for a set of individuals drawn randomly from the reference panels. When the features represent numbers of IBD connections within defined edge weight intervals, the computed feature values are counts calculated by accessing the IBD data in the user data store 145.

The model training module 125 selects the most predictive features (i.e., those estimated to have the highest prediction ability), and removes the remaining features from consideration/use in the model (in some embodiments, this is accomplished simply by setting their corresponding weight or regression coefficient in the model to 0). The number of selected features will vary by implementation, and may vary for each model.

IV.e. Training the Community Classification Model

For each community in the IBD network store 155, the model training module 125 uses the selected features to train 540 the model for that community. Specifically, the model training module 125 uses the set of candidate features selected for that community to train a corresponding model using a supervised machine learning technique. Once training is completed, and the model is saved in the model store 150, the model is able to generate, for a single individual, a score, likelihood or probability for predicting assignment of that individual to the community. In one embodiment, the model outputs a probability (a real number between 0 and 1), in which a number close to 1 indicates that the individual is classified to the community with high confidence, and a number close to 0 indicates with high confidence that the individual is not a member of the community.

The input data to the model training algorithm is the same or similar to the input data provided to the feature selection algorithm above. Individuals that are a part of the community associated with the model being trained are assigned training labels of "1," indicating that they should be classified into the community. Individuals that are part of any other community are assigned training labels of "0," indicating that they should not be classified into the community. In one embodiment, individuals are drawn from reference panels at random to construct the training set provided as input to the model training algorithm and for use in training the model, however in other embodiments the input data may be differently selected. The values for the features used in the training are again the values for those input data individuals.

Any one of a number of supervised learning techniques may be used to train the models. Examples include, but are not limited to, random forests and other ensemble learning techniques, support vector machines (SVM) and logistic regression. Regardless of which supervised learning technique is used, the training process involves determining the numerical values of model parameters so that the model best "fits" the training data. Therefore, the trained model is specified by the fitted values of the model parameters. For example, if a random forests approach is used, the model parameters will consist of the features and splitting criteria that define each decision tree in the random forest model.

Once models have been trained 540, the community identification module 125 stores the models, including the fitted model parameters, in model store 150.

IV.f. Classifying Individuals to Communities Using the Trained Models

The community prediction module 130 uses each trained model to compute, for a given individual, a score, likelihood or probability for assignment of that individual to the community (referred to as classifying the individual or user). The model may be used classify an existing individual, for example someone present in one of the reference panels, or a new user who has submitted their DNA sample for inclusion in the system 100.

The user to be classified has their DNA processed by various parts of the system 100. The user to be classified has their data processed using the genotype identification module 240 and the genotype phasing module 250. In some implementations, the ethnicity estimate module 260 may generate an ethnicity estimate for the user.

The community prediction module 130 then, in conjunction with the IBD estimation module 115, generates IBD estimates between the user and all individuals included in the reference panels stored in the panel store 160. Alternatively, only a subset of those IBD estimates may be generated based on which features and/or individuals are included in the data sets used to train the models. This can reduce processing costs in generating community classification predictions, as it may not be necessary to know all IBD estimates when the models only make use of some fraction of them.

For a single input individual, the community prediction module 130 compiles the IBD estimates (and, in some instances, the ethnicity estimates) into feature vectors according to the features selected for each of the models. Each model will receive a different feature vector depending on which features were selected and used to train that particular model. Thus, the estimated IBD that is relevant to the community classification will be different for each model (and hence, for each community).

The community prediction module 130 then computes a score, probability or likelihood for each model. In one implementation, an individual is classified as belonging a given community if the probability computed by the trained model exceeds a threshold numerical value. The threshold for classifying individuals to communities may be the same or different for each model. The output of the community prediction module includes both the classification and score/probability/likelihood for each community.

Due to a variety of factors such as the broad genetic diversity of the user base, the varying quality of the IBD estimates for different users, and the heterogeneity in composition of the communities identified in the IBD network, an individual may be predicted to be a member of zero, one, or more communities. In one embodiment, the output of the community prediction module may be reported to a user via a generated document or a GUI. Data reported in the document or GUI may also draw on annotations associated with the community, as well as historical or geographic interpretations drawing from summaries of the annotations associated with the community. This may include geographical features or regions distinguishing the community, and other historical, social or economic features characteristic of the community that may or may not be informed by the annotations. The community assignment module 135 may additionally produce reports that summarize IBD connections and other genetic estimates relevant to each community; for example, an estimate of the number of 2nd cousins that are classified as belonging to the same community as the user.

V. Additional Considerations

Computing system 100 is implemented using one or more computers having one or more processors executing application code to perform the steps described herein, and data may be stored on any conventional non-transitory storage medium and, where appropriate, include a conventional database server implementation. For purposes of clarity and because they are well known to those of skill in the art, various components of a computer system, for example, processors, memory, input devices, network devices and the like are not shown in FIG. 1. In some embodiments, a distributed computing architecture is used to implement the described features. One example of such a distributed computing platform is the Apache Hadoop project available from the Apache Software Foundation.

In addition to the embodiments specifically described above, those of skill in the art will appreciate that the invention may additionally be practiced in other embodiments. Within this written description, the particular naming of the components, capitalization of terms, the attributes, data structures, or any other programming or structural aspect is not mandatory or significant unless otherwise noted, and the mechanisms that implement the described invention or its features may have different names, formats, or protocols. Further, the system may be implemented via a combination of hardware and software, as described, or entirely in hardware elements. Also, the particular division of functionality between the various system components described here is not mandatory; functions performed by a single module or system component may instead be performed by multiple components, and functions performed by multiple components may instead be performed by a single component. Likewise, the order in which method steps are performed is not mandatory unless otherwise noted or logically required. It should be noted that the process steps and instructions of the present invention could be embodied in software, firmware or hardware, and when embodied in software, could be downloaded to reside on and be operated from different platforms used by real time network operating systems.

Algorithmic descriptions and representations included in this description are understood to be implemented by computer programs. Furthermore, it has also proven convenient at times, to refer to these arrangements of operations as modules or code devices, without loss of generality.

Unless otherwise indicated, discussions utilizing terms such as "selecting" or "determining" or "estimating" or the like refer to the action and processes of a computer system, or similar electronic computing device, that manipulates and transforms data represented as physical (electronic) quantities within the computer system memories or registers or other such information storage, transmission or display devices.

Finally, it should be noted that the language used in the specification has been principally selected for readability and instructional purposes, and may not have been selected to delineate or circumscribe the inventive subject matter. Accordingly, the disclosure of the present invention is intended to be illustrative, but not limiting, of the scope of the invention.

The invention claimed is:

1. A method comprising:
   obtaining a DNA sample from an individual;
   determining the genotype of the individual based on the DNA sample;
   accessing, from a non-transitory computer readable storage medium of a computing device, a plurality of reference panels each associated with one of a plurality of different communities, each community comprising a plurality of nodes, each node corresponding to a reference genotype of a different reference individual;
   determining, with a computer processor associated with the computing device, amounts of DNA overlap between the genotype and each of the reference panels;
   for each reference panel, inputting the amount of DNA overlap between the genotype and the reference panel into a model specific for a community associated with the reference panel to generate a score for the community with respect to the genotype, the model comprising a first set of features defined from amounts of DNA overlap between reference individuals in the reference panel of that community and a second set of features defined as the number of connections between the individual and individuals in one of the reference panels within specified ranges of amounts of estimated IBD; and
   generating, with the computer processor, a report summarizing the communities for which the individual's score exceeds a threshold.

2. The method of claim 1, wherein the nodes of each community are connected via edges with weights based on IBD estimates between the genotypes of the reference individuals.

3. The method of claim 2, wherein the reference individuals and their corresponding nodes are grouped into the reference panels based on the edge weights between nodes.

4. The method of claim 2, wherein an IBD estimate is an amount DNA overlapping between the genotype of one individual and the genotype of another individual.

5. The method of claim 4, wherein an IBD estimate is a total amount of one or more chromosomes that is inherited from an ancestor that is common to the given individual and one of individuals in one of the reference panels.

6. The method of claim 1, wherein the model further comprises separate features for each of the specified ranges for each of the different reference panels.

7. The method of claim 1 further comprising:
   generating an IBD network comprising the communities and associated reference panels by:
   generating a plurality of IBD estimates, each IBD estimate being between each of a pair of individuals in one of the reference panels;
   mapping the IBD estimates into edge weights:
   applying a network clustering algorithm to the network defined by these edge weights to identify two or more communities; and
   classifying the individuals to each community based on the IBD estimates.

8. The method of claim 1, further comprising:
   accessing pedigree information regarding the reference panel individuals, the pedigree information specifying information about ancestors of the reference panel individuals.

9. The method of claim 8, further comprising:
   annotating the communities with at least one of ancestral birth location labels and surname labels based on the pedigree information of the reference panel individuals associated with each community; and
   wherein generating the report further comprises sending a summary based on at least one of the birth location labels and the surname labels for the communities when the individual's score exceeds the threshold.

10. The method of claim 1, further comprising:
generating ethnicity estimates for the reference panel individuals;
annotating the communities with ethnicity labels based on the ethnicity estimates associated with the reference panel associated with each community; and
wherein generating the report further comprises sending a summary based on the ethnicity labels for the communities when the individual's score exceeds the threshold.

11. A non-transitory computer readable storage medium comprising computer program instructions that when executed by a processor cause the processor to:
obtain a DNA sample from an individual;
determine the genotype of the individual based on the DNA sample;
access, from a non-transitory computer readable storage medium of a computing device, a plurality of reference panels each associated with one of a plurality of different communities, each community comprising a plurality of nodes, each node corresponding to a reference genotype of a different reference individual;
determine, with a computer processor associated with the computing device, amounts of DNA overlap between the genotype and each of the reference panels;
for each reference panel, input the amount of DNA overlap between the genotype and the reference panel into a model specific for the community associated with the reference panel to generate a score for the community with respect to the genotype, the model comprising a first set of features defined from amounts of DNA overlap between reference individuals in the reference panel of that community and a second set of features defined as the number of connections between the individual and individuals in one of the reference panels within specified ranges of amounts of estimated IBD; and
generate, with the computer processor, a report summarizing the communities for which the individual's score exceeds a threshold.

12. The medium of claim 11, wherein the nodes of each community are connected via edges with weights based on IBD estimates between the genotypes of the reference individuals.

13. The medium of claim 12, wherein the reference individuals and their corresponding nodes are grouped into the reference panels based on the edge weights between nodes.

14. The medium of claim 12, wherein an IBD estimate is an amount DNA overlapping between the genotype of one individual and the genotype of another individual.

15. The medium of claim 14, wherein an IBD estimate is a total amount of one or more chromosomes that is inherited from an ancestor that is common to the given individual and one of individuals in one of the reference panels.

16. The medium of claim 11, wherein the model further comprises separate features for each of the specified ranges for each of the different reference panels.

17. The medium of claim 11, wherein the instructions further cause the processor to:
generate an IBD network comprising the communities and associated reference panels by:
generating a plurality of IBD estimates, each IBD estimate being between each of a pair of individuals in one of the reference panels;
mapping the IBD estimates into edge weights:
applying a network clustering algorithm to the network defined by these edge weights to identify two or more communities; and
classifying the individuals to each community based on the IBD estimates.

18. The medium of claim 11 wherein the instructions further cause the processor to:
access pedigree information regarding the reference panel individuals, the pedigree information specifying information about ancestors of the reference panel individuals.

19. The medium of claim 18 wherein the instructions further cause the processor to:
annotate the communities with at least one of ancestral birth location labels and surname labels based on the pedigree information of the reference panel individuals associated with each community; and
wherein generating the report further comprises sending a summary based on at least one of the birth location labels and the surname labels for the communities when the individual's score exceeds the threshold.

20. The medium of claim 11 wherein the instructions further cause the processor to:
generate ethnicity estimates for the reference panel individuals;
annotate the communities with ethnicity labels based on the ethnicity estimates associated with the reference panel associated with each community; and
wherein the instructions that cause the processor to generate the report further comprises instructions that cause the processor to send a summary based on the ethnicity labels for the communities when the individual's score exceeds the threshold.

* * * * *

UNITED STATES PATENT AND TRADEMARK OFFICE
CERTIFICATE OF CORRECTION

PATENT NO. : 9,940,433 B2
APPLICATION NO. : 15/458549
DATED : April 10, 2018
INVENTOR(S) : Eunjung Han, Ross E. Curtis and Peter Carbonetto

It is certified that error appears in the above-identified patent and that said Letters Patent is hereby corrected as shown below:

In the Claims

Column 18, Claim 4, Line 32: after amount, insert -- of --;

Column 19, Claim 14, Line 50: after amount, insert -- of --.

Signed and Sealed this
Fourth Day of June, 2019

Andrei Iancu
*Director of the United States Patent and Trademark Office*